United States Patent
Lee et al.

(10) Patent No.: US 10,265,524 B2
(45) Date of Patent: Apr. 23, 2019

(54) ELECTRICAL STIMULATION SYSTEM FOR RECOGNIZING BRAIN ACTIVATION PATTERN AND APPLYING ELECTRICAL STIMULATION TO A USER

(71) Applicant: YBRAIN INC., Seoul (KR)

(72) Inventors: Kiwon Lee, Daejeon (KR); Kyongsik Yun, Daejeon (KR); Seungyeon Kim, Seoul (KR)

(73) Assignee: YBRAIN INC., Seoul (KR)

( * ) Notice: Subject to any disclaimer, the term of this patent is extended or adjusted under 35 U.S.C. 154(b) by 798 days.

(21) Appl. No.: 14/745,359

(22) Filed: Jun. 19, 2015

(65) Prior Publication Data
US 2015/0367129 A1    Dec. 24, 2015

(30) Foreign Application Priority Data
Jun. 20, 2014    (KR) ......................... 10-2014-0075855

(51) Int. Cl.
*A61N 1/36*    (2006.01)
*A61N 1/04*    (2006.01)

(52) U.S. Cl.
CPC ....... *A61N 1/36025* (2013.01); *A61N 1/0492* (2013.01)

(58) Field of Classification Search
CPC ................... A61N 1/0492; A61N 1/36025
See application file for complete search history.

(56) References Cited

FOREIGN PATENT DOCUMENTS

| KR | 20080107961 A | 12/2008 |
| KR | 101094350 B | 12/2011 |
| KR | 101473456 B1 | 10/2014 |

OTHER PUBLICATIONS

Korean Office Action dated Aug. 27, 2014 for corresponding Korean Application No. 10-2014-0075855, citing the references above.

*Primary Examiner* — Amanda K Hulbert
(74) *Attorney, Agent, or Firm* — Studebaker & Brackett PC

(57) ABSTRACT

The present disclosure relates to an accounting method for electrical stimulation apparatus, comprising, in accordance with one exemplary embodiment of the present invention, receiving an information on authority for use of an electrical simulation apparatus from a second apparatus if a signal for payment request for the authority for use of the electrical simulation apparatus received from a first apparatus is processed and the information on the authority for use of the electrical stimulation apparatus is transmitted to a second apparatus; operating the electrical stimulation apparatus on the basis of the received information on the authority for use; collecting details of usage of the electrical stimulation apparatus; analyzing the collected details of usage; and renewing the received information on the authority for use on the basis of the analyzed details of usage.

5 Claims, 7 Drawing Sheets

ELECTRICAL STIMULATION SYSTEM FOR RECOGNIZING BRAIN ACTIVATION PATTERN AND APPLYING ELECTRICAL STIMULATION TO A USER

CROSS-REFERENCE TO RELATED APPLICATION

This application claims the priority of the Korean Patent Application No. 10-2014-0076052, filed on Jun. 20, 2014 in the Korean Intellectual Property Office (KIPO), and all the benefits accruing therefrom under 35 U.S.C. § 119, the contents of which in their entirety are herein incorporated by reference.

TECHNICAL FIELD

The present invention relates to an accounting method for electrical stimulation apparatus, and more particularly, to an accounting method for electrical stimulation apparatus applying electrical stimulation to a part of a user's body.

BACKGROUND ART

The brain is the highest nucleus organ of the nervous system, placed inside the head. The brain consists of cerebrum, cerebellum, midbrain (mesencephalon), pons, and medulla, and generates brainwaves. The brainwave, as also known as electroencephalography (EEG), is a current of electricity generated in the course of transmission of signals between the brain nerves in the nervous system. The brainwave differs depending on physical and mental conditions, and is the most important indicator for measuring brain activity.

Applying electrical stimulation to brain may help relieve or alleviate neurological symptom such as hand tremor. There are invasive and noninvasive methods for electrical stimulation of the brain. The invasive method is to insert the electrode into the brain by operation and to transmit the electrical signals to the electrode. On the other hand, the noninvasive method is to attach the electrode to scalp, and transmit the electrical signal to the electrode.

The noninvasive electrical stimulation has an advantage of lower cost and risk than the invasive method. Therefore, research and development about the noninvasive electrical stimulation of the brain has been carried out.

Meanwhile, such electrical stimulation apparatus can be sold through many different structures. For example, the structure of manufacturer-distributor-customer, or of manufacturer-customer can be available.

According to such sales structures, however, the problem is that they charge full payment of the sale price even for the user not actively using the electrical stimulation apparatus regardless of the frequency of use.

For the user actively using the electrical stimulation apparatus the manufacturer cannot charge extra payment for the various usages the user may have for himself, someone else's brain, or for the parts of the body other than the brain.

RELATED DOCUMENT

Patent Document (Patent 1) Korean Patent No. 10-10094359 (Title of Invention: Multiple Bio-stimulation check analysis system, Dec. 8, 2011)

DISCLOSURE OF INVENTION

Technical Problem

The present invention seeks to provide the accounting method for electrical stimulation apparatus by which both the manufacturer and the user of the electrical stimulation apparatus can ensure benefits.

Advantageous Effects

Charging on the basis of the details of usage of the electrical stimulation apparatus ensures benefits both of the manufacturer and the user.

The accounting method for electrical stimulation apparatus can be varied because a requester that requests a payment for the authority for use of the electrical stimulation apparatus, a payer that makes a requested payment, and a user who receives the authority for use and uses the apparatus can be separately set up.

Due to various accounting methods, the electrical stimulation apparatus can be more widely used.

DETAILED DESCRIPTION

Figure 1:
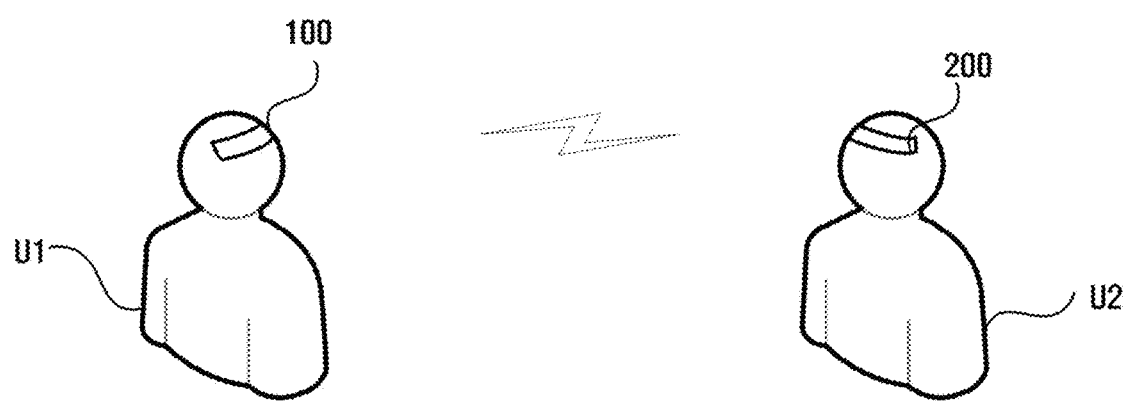
FIG. 1 is a diagram illustrating a composition of electrical stimulation system according to one exemplar, embodiment.

A desirable exemplary embodiment of the present invention will be described in detail hereinafter in reference with the accompanied drawings. The advantage and characteristic, and a method to achieve them will be obvious upon detailed description of the exemplary embodiments as well as accompanied drawings which follow. However, the present invention is not limited to the exemplary embodiments set forth herein, but can be embodied in many different forms. The exemplary embodiments are provided only to render the present disclosure complete and the scope of the present invention comprehensible to those having ordinary skill in the art. The present invention is only to be defined by the claims. A same reference mark used refers to a same element throughout the description.

Without separate definitions, all terms (including technical and scientific terms) used in the present description may be used for the meanings commonly understandable to those having ordinary skill in the art. In addition, the terms generally used and having definitions in dictionary, unless otherwise defined obviously in particular, should not be ideally or exaggeratedly interpreted.

The terms used in the present description are to explain the exemplary embodiments, not to limit the present invention thereto. In the present description, a singular form of word also includes a plural form thereof unless otherwise noted. The term "comprises" and/or "comprising" is not excluding the meaning that one or more elements other than the said element may exist or be added.

In reference with the accompanying drawings, the exemplary embodiments of the present invention are to be described. Each reference numeral is used consistently throughout the drawings.

FIG. 1 is a diagram illustrating an accounting system and method according to one exemplary embodiment.

According to FIG. 1, the accounting system according to one exemplary embodiment may include an electrical stimulation apparatus (400) and an accounting processing apparatus (300).

The electrical stimulation apparatus (400), contacted to a particular part of a user (U)'s body, may apply electrical stimulation to the particular part, or measure signals therefrom. For example, the electrical stimulation apparatus (400), contacted to one of the body parts selected from the group consisting of brain, arm, leg, and shoulder, can apply electrical stimulation to the selected area or measure signals therefrom.

In order for this, the electrical stimulation apparatus (400) may have a wearable form. For example, the electrical stimulation apparatus (400) may be a form of helmet which can be worn on the head. For another example, the electrical stimulation apparatus (400) may be a form of band which entirely surrounds the circumference of head, arm, or leg. The electrical stimulation apparatus (400) with a form of bracelet surrounding a part of the circumference of arm or leg can be another example. Or, the electrical stimulation apparatus (400) with a form of patch adhering to skin surface can also be another example. Below, the case the electrical stimulation apparatus (400) applies electrical stimulation to the brain of the user (U) or measures the brainwaves will be explained as an example.

Figure 2:
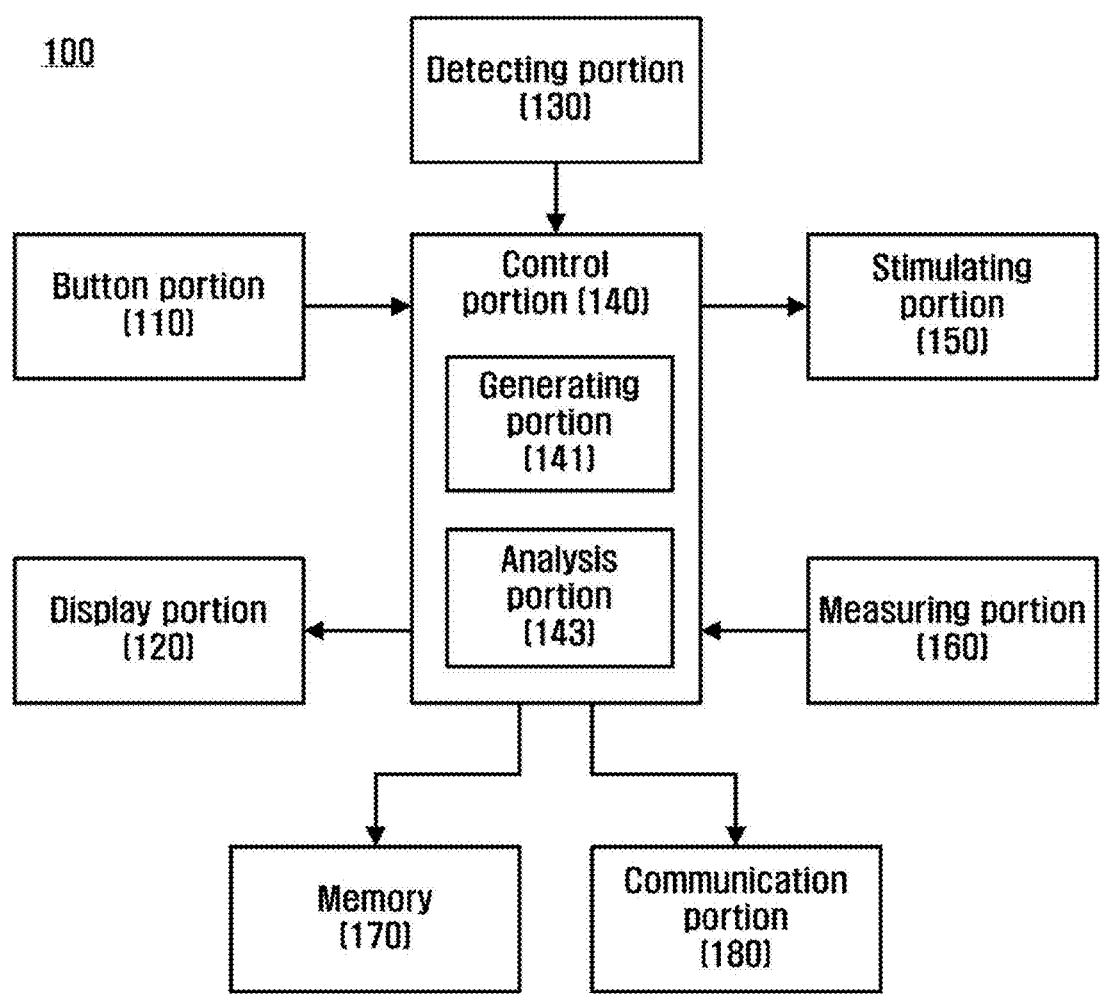
FIG. 2 is a diagram illustrating a composilion of Ihc first electrical stimulation apparatus (100) of Figure 1.

FIG. 2 is a diagram illustrating a control configuration of the electrical stimulation apparatus (400) according to one exemplary embodiment.

According to FIG. 2, the electrical stimulation apparatus (400) may include an electrode portion (410), a button portion (430), a power supply portion (440), a control portion (420), and a communication portion (450).

An electrode portion (410) may include a plurality of electrodes adhered to the user (U)'s head. Particularly, the electrode portion (410) may include a ground electrode (411), a reference electrode (412), and an active electrode (413).

A ground electrode (411) can carry out a role of matching a reference potential of the electrical stimulation apparatus (400) with that of a human body. The ground electrode (411) may be adhered to the area in which the brainwaves are weak or not measured; for example, the root of the right ear.

A reference electrode (412) may also be adhered to the area in which the brainwaves are weak or not measured like the ground electrode (411). For example, the reference electrode (412) can be adhered to the same area as the ground electrode (411). For another example, the reference electrode (412) can be adhered to different areas. Particularly, in case the ground electrode (411) is adhered to the root of the right ear, the reference electrode (412) may be adhered to the root of the left ear, back of neck, or cheek.

An active electrode (413) can be adhered to the user (U)'s scalp. A plurality of active electrodes (413) can be arranged. Although not shown by the drawing, the active electrode (413) may include a measuring electrode and a stimulating electrode. The measuring electrode, used for measuring brainwaves, can be adhered to a first area of the user (U)'s head. The stimulating electrode, used for applying electrical stimulation to brain, can be adhered to a second area of the user (U)'s head. The first and second area may or may not be the same.

According to one exemplary embodiment, the measuring electrode is differentiated from the stimulating electrode only by function; the two may be the same electrodes physically. In this case, measuring brainwaves from the user (U)'s brain and applying electrical stimulation thereto may be performed in order.

According to another exemplary embodiment, the measuring electrode and the stimulating electrode may be different from each other not only in function but also physically. In this case, measuring brainwaves from the user (U)'s brain and applying electrical stimulation thereto can be performed at the same time.

A button portion (430) is a place where the user (U) enters command. In order for that, the button portion (430) may include at least one button. For example, the button portion (430) may include at least one selected from the group consisting of a power supply button, a brainwave measuring execution button, an electrical stimulation execution button, a stimulation strength control button, and a stimulation time control button. But the kind of button is not limited to the buttons exemplified.

A power supply portion (440) can supply power to the electrode portion (410) or a control portion (420) which follows. The power supply portion (440) may be embodied as a form integral with the electrical stimulation apparatus (400) or physically separable therefrom.

A control portion (420) can process the command entered by the button portion (430).

For example, when the brainwave measuring execution button is authorized, the control portion (420) can collect the brainwave signal measured by the measuring electrode of the electrode portion (410). In order for this, the control portion (420) may include at least one selected from the group consisting of a current-voltage converter which converts the current signal, measured by at least one measuring electrode, to the voltage signal; an amplifier which amplifies the voltage signal; a filter which removes noises from the amplified voltage signal; and an A/D (analog to digital) converter which converts the noise-removed voltage signal from analog to digital.

For another example, when the electrical stimulation execution button authorized, the control portion (420) can authorize the voltage to the stimulating electrode of the electrode portion (410) on the basis of the strength and time for stimulation set up by the user (U). In order for this, the control portion (420) may further include a voltage supply portion supplying voltage to a plurality of stimulating electrodes.

Besides, the control portion (420) can collect the details of usage of the electrical stimulation apparatus (400) when the user (U) uses (S10) the electrical stimulation apparatus (400). At this, the details of usage may include at least one selected from the group consisting of the number of electrical stimulation applied to the user, the strength of electrical stimulation, and the time for electrical stimulation applied. However the details of usage are not limited thereto.

A communication portion (450) transmits (S11) the details of usage collected by the control portion (420) to the accounting processing apparatus (300). For example, the communication portion (450) can transmit the details of usage to the accounting processing apparatus (300) by wired or wireless method of communication.

According to FIG. 1, the accounting processing apparatus (300) can analyze (S12) the details of usage of the electrical stimulation apparatus (400) received from the electrical stimulation apparatus (400). And on the basis of the result of analysis, the accounting process for the usage of the electrical stimulation apparatus (400) can be performed (S13). In order for this, the accounting processing apparatus (300) may include a communication portion (310), an analysis portion (320), and an accounting processing portion (330).

A communication portion (310) can transmit and receive data and/or signals to/from the communication portion (450) of the electrical stimulation apparatus (400). The communication portion (310) of the accounting processing apparatus (300) can receive the details of usage from the electrical stimulation apparatus (400) by wired or wireless method of communication. The received details of usage can be provided to an analysis portion (320) which follows.

An analysis portion (320) can analyze the details of usage of the electrical stimulation apparatus (400). According to one exemplary embodiment, the analysis portion (320) can analyze which level each item corresponds to among the pre-set levels by item. For example, total three levels may exist from level 1, level 2, to level 3 regarding the number of electrical stimulation applied. At this, in case the number of electrical stimulation applied by the electrical stimulation apparatus (400) is ranged from 1 to 10, the amount of use related to the number of electrical stimulation applied may belong to level 1. In case the number of electrical stimulation applied is ranged from 11 to 20, the amount of use related to the number of electrical stimulation may fall into level 2. The analysis portion (320) can also perform the analysis in the same manner for the strength of electrical stimulation and the time for electrical stimulation applied, respectively.

After this, the analysis portion (320) can set different rates for each level. According to the exemplary embodiment, the higher rate may be charged as the level increases. For example, the rate set for each level shows linear increase as the level increases. For another example, the rate set for each level shows nonlinear increase as the level increases. The information on the level of the amount of usage for each item among the details of usage of the electrical stimulation apparatus (400) can be provided to an accounting processing portion (330) which will be described thereinafter.

According to another exemplary embodiment, the analysis portion (320) can apply a different weighted value for each item of the details of usage. For example, the weighted value 1, 2, 3 can be applied for the number of electrical stimulation applied, the strength of electrical stimulation applied, and the time for electrical stimulation applied, respectively. In this case, the information on levels which each item belongs to and on the weighted value for each item can be provided to an accounting processing portion (330).

An accounting processing portion (330), on the basis of the result of analysis received from the analysis portion (320), can perform accounting process for the use of the electrical stimulation apparatus (400). For example, in case the information on the levels which the amount of usage for each item belongs to is provided by the analysis portion (320), the accounting processing portion (330) can add up the rates corresponding to the levels received, and charge the total rate for the use of the electrical stimulation apparatus (400) to the user. When the user of the electrical stimulation apparatus (400) pays the charge, the accounting processing portion (330) can transmit the relevant amount to the manufacturer of the electrical stimulation apparatus (400).

For another example, in case the information on the levels which the amount of use for each item belongs to and on the weighted value for each item are provided by the analysis portion (320), the accounting processing portion (330) multiplies the rate for each item corresponding to each level by the weighted value for each item, respectively, and then adds up the rates multiplied by the weighted values. And finally the total rate can be charged to the user of the electrical stimulation apparatus (400). When the user of the electrical stimulation apparatus (400) pays the charge, the accounting processing portion (330) can transmit the relevant amount to the manufacturer of the electrical stimulation apparatus (400).

Above, the accounting system and method according to one exemplary embodiment were described in reference with FIGS. 1 and 2. FIG. 1 shows the example of the control portion (320) included in the accounting processing apparatus (300), but the present invention is not limited thereto. For example, the control portion (320) may be included in the electrical stimulation apparatus (400). For another example, the control portion (320) may be included in a first apparatus (not shown) capable of communicating with the electrical stimulation apparatus (400).

Figure 3:
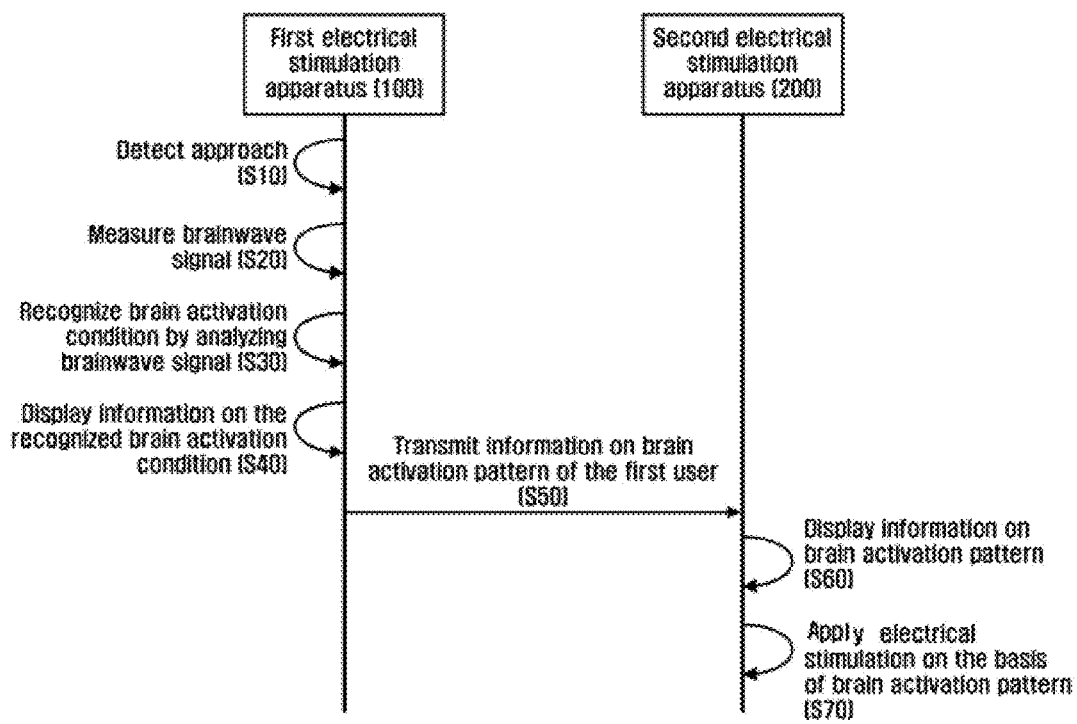
FIG. 3 is a flow chart illustrating a method for electrical stimulation by the electrical stimulation system of FIG. I.

FIG. 3 is a diagram illustrating the accounting system and method according to another exemplary embodiment.

In reference with FIG. 3, the accounting system according to another exemplary embodiment may include a first apparatus (100), the accounting processing apparatus (300), a second apparatus (200), and the electrical stimulation apparatus (400). At this, the first apparatus (100) is a device which a first user (U1) uses. The second apparatus (200) and the electrical stimulation apparatus (400) are the devices which a second user (U2) uses.

A first apparatus (100) can transmit the signal for payment request for authority for use of the electrical stimulation apparatus (400) according to the command of a first user (U1) to the accounting processing apparatus (300). The first apparatus (100) may include a wired and wireless communication device. The examples for a communication device include a mobile device such as a Cellular phone, a PCS phone (Personal Communication Service phone), and a synchronous/asynchronous IMT-2000 (International Mobile Telecommunication-2000), a Palm PC (Personal Computer), a PDA (Personal Digital Assistant), a Smart phone, a WAP phone (Wireless application protocol phone), and a mobile play-station. Such first apparatus (100) may include, although not shown by the drawing, an input portion for receiving a command from the first user (U1), a processing portion for processing the received command, a display portion for displaying the status of processing the command, and a communication portion for communicating with the accounting processing apparatus (300).

According to the exemplary embodiment, the signal for payment request may include the information on the authority for use of the electrical stimulation apparatus (400), the requester that requested the payment for the authority for use, the payer that actually pays the charge, and on the authorized user that receives the information about the authority for use.

At this, the information on the payment requester may be the identification information of the apparatus requesting the payment. In case of FIG. 3, the payment requester means the first apparatus (100).

The information on the payer may be the identification information of the apparatus to which the requested rate is charged. According to FIG. 3, the payer can be the first apparatus (100) or the second apparatus (200).

The information on the authorized user may be the identification information of the apparatus which receives the information about the authority for use with a complete payment. According to FIG. 3, the authorized user means the first apparatus (100).

According to one exemplary embodiment, the information on the authority for use of the electrical stimulation apparatus (400) may be the rate information on the authority for use. For example, the rate information on the authority for use may be one selected by the first user (U1) among many rate information displayed by the first apparatus (100). For another example, the rate information on the authority for use may be the one directly entered by the user.

According to another exemplary embodiment, the information on the authority for use may be the information on the kind of authority for use and its setting. For the kind of authority for use, the authority for use regarding the number of electrical stimulation applied and the strength thereof, and the time for electrical stimulation applied can be exemplified.

The kind of authority for use exemplified above can be displayed by the first apparatus (100). And the first user (U1) can select at least one among the displayed authority for use, and set up the value for the selected authority for use. For example, the first user (U1) can select the number of electrical stimulation to be applied and set up the value as 10. For another example, the first user (U1) can select the strength of electrical stimulation to be applied, and set up the value as much as he/she wants. For another example, the first user (U1) can select the time for electrical stimulation to be applied, and set up the time in a certain unit as he/she wants. At this, the user can set up the time period for electrical stimulation to be applied at a time, total time available for use of the electrical simulation apparatus (400), or both.

Once entered all the information including the authority for use of the electrical stimulation apparatus (400); the payment requester that requests a payment for the authority for use; the payer that actually pays the charge; and the authorized user that receives the authority for use with a complete payment, the first apparatus (100) generates the signal for payment request including the entered information above, and transmits (S21) the signal to the accounting processing apparatus (300).

The accounting processing apparatus (300) can receive the signal for payment request from the first apparatus (100), and perform accounting process (S22) on the basis of the received signal for payment request, and transmit (S23) the information on the authority for use with a complete payment to the second apparatus (200). For this, the accounting processing apparatus (300) may include a communication portion (310) and an accounting processing portion (330).

A communication portion (310) can communicate with the first apparatus (100) and the second apparatus (200). Particularly, the communication portion (310) can receive the signal for payment request for the authority for use of the electrical stimulation apparatus (400) from the first apparatus (100), and transmit the authority for use with a complete payment to the second apparatus (200). At this, the communication portion (310) can communicate with the first apparatus (100) and the second apparatus (200) by wired or wireless method of communication.

An accounting processing portion (330), on the basis of the signal for payment request received from the first apparatus (100), can perform accounting process for the authority for use of the electrical stimulation apparatus (400). Particularly, the accounting processing portion (330) can charge the rate to the payer: the rate on the basis of the information on the authority for use among the information included in the signal for payment request, or the rate calculated on the basis of the information on the authority for use.

Next, the accounting processing portion (330), on the basis of the signal for payment request received from the first apparatus (100), can transmit the authority for use with a complete payment to the authorized user.

The second apparatus (200) can receive the information on the authority for use with a complete payment from the accounting processing portion (300), and transmit (S24) it to the electrical stimulation apparatus (400). The second apparatus (200) may include a wired and wireless communication device; the examples for a communication device include a mobile device such as a Cellular phone, a PCS phone (Personal Communication Service phone), and a synchronous/asynchronous IMT-2000 (International Mobile Telecommunication-2000), and a Palm PC (Personal Computer), a PDA (Personal Digital Assistant), a Smart phone, a WAP phone (Wireless application protocol phone), and a mobile play-station. Such second apparatus (200) may include, although not shown by the drawing, an input portion for receiving a command from the second user (U2), a processing portion for processing the received command, a display portion for displaying the status of processing the command, and a communication portion for communicating with the accounting processing apparatus (300) or the electrical stimulation apparatus (400).

According to one exemplary embodiment, in case the command is received from the second user (U2), the second apparatus (200) can transmit (S24) the information on the authority for use received from the accounting processing apparatus (300) to the electrical stimulation apparatus (400).

According to another exemplary embodiment, in case the information on the authority for use received from the accounting processing apparatus (300), the second apparatus (200) can automatically transmit (S24) the received information on the authority for use to the electrical stimulation apparatus (400). In order for this, the information of the electrical stimulation apparatus (400) can be registered in the second apparatus (200) in advance. For example, as the pairing process between the second apparatus (200) and the electrical stimulation apparatus (400) is performed by Bluetooth or Near Field Communication (NFC), the information of the second apparatus (200) can be registered on the electrical stimulation apparatus (400), and vice versa.

The electrical stimulation apparatus (400) can receive the information on the authority for use from the second apparatus (200), and operate (S25) on the basis of the received information on the authority for use. For example, in case the information on the authority for use received from the second apparatus (200) includes the rate information, the electrical stimulation apparatus (400) can calculate the rate for the use on the basis of the strength and the time for the stimulation applied whenever the electrical stimulation is applied to the second user (U2), and deduct the amount calculated from the received rate information.

Figure 4:
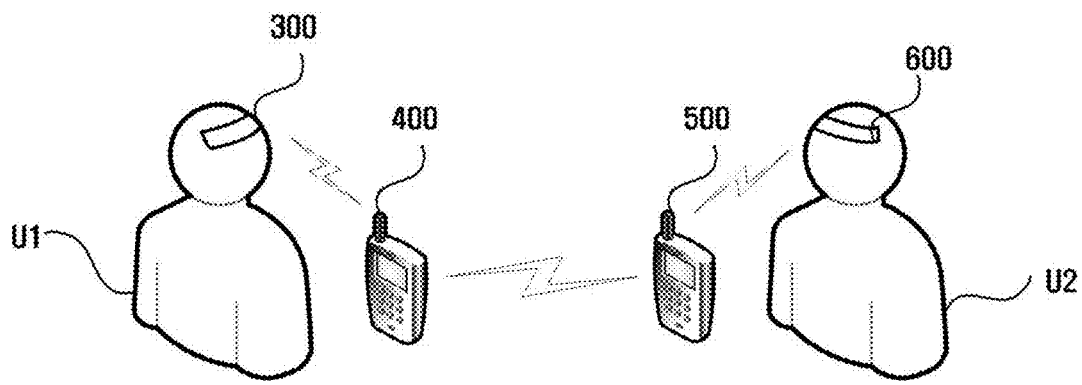
FIG. 4 is a diagram illustrating a composition of the electrical stimulation system according to another exemplary embodiment.

For another example, in case the information on the authority for use received from the second apparatus (200)

includes the information on the kind of authority for use and its setting, the electrical stimulation apparatus (400) may operate on the basis of this information on the kind of the authority for use and its setting. For example, when the kind of the authority for use is related to the number of stimulation which is set up as 10, the set number may be deducted one by one whenever the second user (U2) uses the electrical stimulation apparatus (400) to apply electrical stimulation Above, in reference with FIG. 3 the accounting system and method according to another exemplary embodiment was described. FIG. 3 shows the case the first apparatus (100) and the second apparatus (200) are different from each other. According to another exemplary embodiment, the first apparatus (100) and the second apparatus (200) may be the same. FIG. 4 can be referred for more details about this.

FIG. 4 is a diagram illustrating the accounting system and method according to further exemplary embodiment.

In reference with FIG. 4, the accounting system according to further exemplary embodiment may include the second apparatus (200), the accounting processing apparatus (300), and the electrical stimulation apparatus (400).

The second apparatus (200) can transmit a signal for payment request for the authority for use of the electrical stimulation apparatus (400) according to the command of the second user (U2). The second apparatus (200), although not shown by the drawing, may include an input portion for receiving a command from the second user (U2), a processing portion for processing the received command, a display portion for displaying the result of processing the command, and a communication portion for communicating with the accounting processing apparatus (300).

The second user (U2), using the second apparatus (200), can enter the information on the authority for use of the electrical stimulation apparatus (400), on the payment requester that charges for the authority for use, on the payer that actually pays the charge, and the information on the authorized user that receives the authority for use with a complete payment.

When all the above mentioned information entered, the second apparatus (200) can generate the signal for payment request including the entered information, and transmit (S31) it to the accounting processing apparatus (300).

A communication portion (310) of the accounting processing apparatus (300) can receive the signal for payment request from the second apparatus (200). When the signal for payment request received, the accounting processing portion (330) of the accounting processing apparatus (300) can perform (S32) accounting process on the basis of the received signal for payment request. When the process finished, the accounting processing apparatus (300) can transmit (S33) the information on the authority for use with a complete payment to the second apparatus (200) by the communication portion (310).

The second apparatus (200) can receive the information on the authority for use with a complete payment from the accounting processing apparatus (300), and transmit (S34) it to the electrical stimulation apparatus (400). At this, the second apparatus (200) can transmit the information on the authority for use to the electrical stimulation apparatus (400) by wired or wireless method of communication.

According to one exemplary embodiment, in case the command of the second user (U2) is entered, the second apparatus (200) can transmit (S34) the information on the authority for use received from the accounting processing apparatus (300) to the electrical stimulation apparatus (400).

According to another exemplary embodiment, in case the information on the authority for use is received from the accounting processing apparatus (300), the second apparatus (200) can automatically transmit (S34) the received information on the authority for use to the electrical stimulation apparatus (400). In order for this, the pairing process between the second apparatus (200) and the electrical stimulation apparatus (400) may be performed in advance to register each other's information.

The electrical stimulation apparatus (400) can receive the information on the authority for use from the second apparatus (200), and operate (S35) on the basis of the received information on the authority for use.

Figure 5:
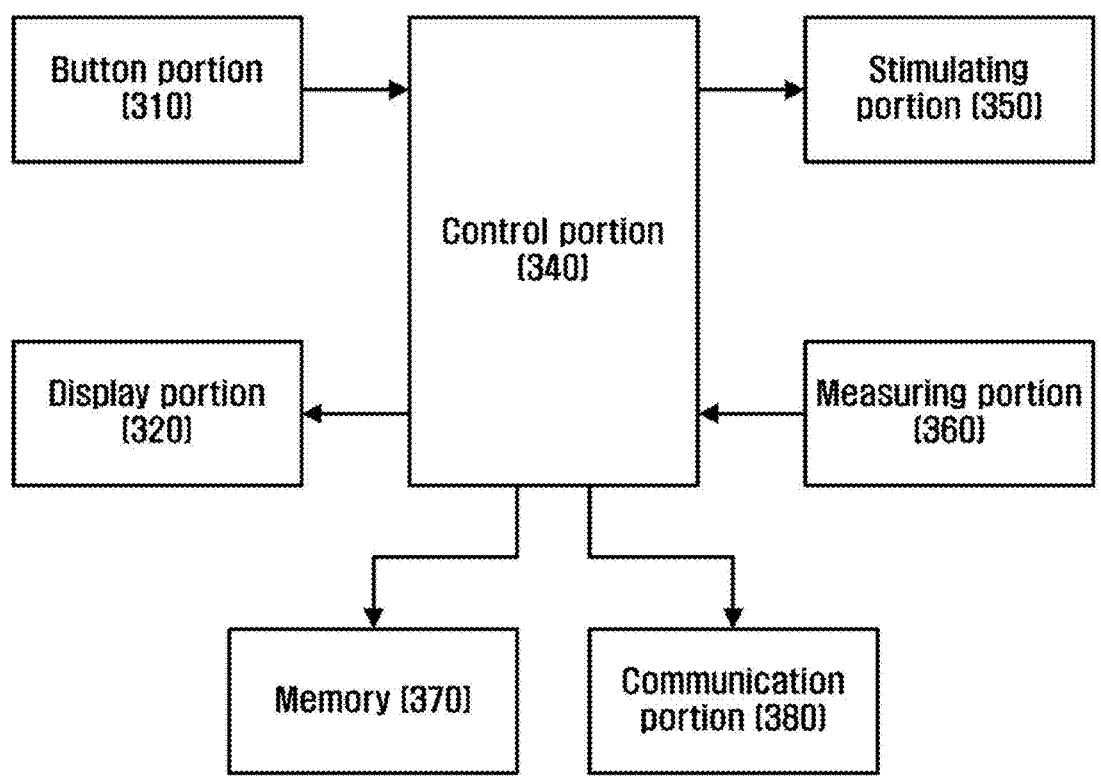
FIG. 5 is a diagram illustrating a composition of the first electrical stimulation apparatus (300) of FIG. 4.
Figure 6:
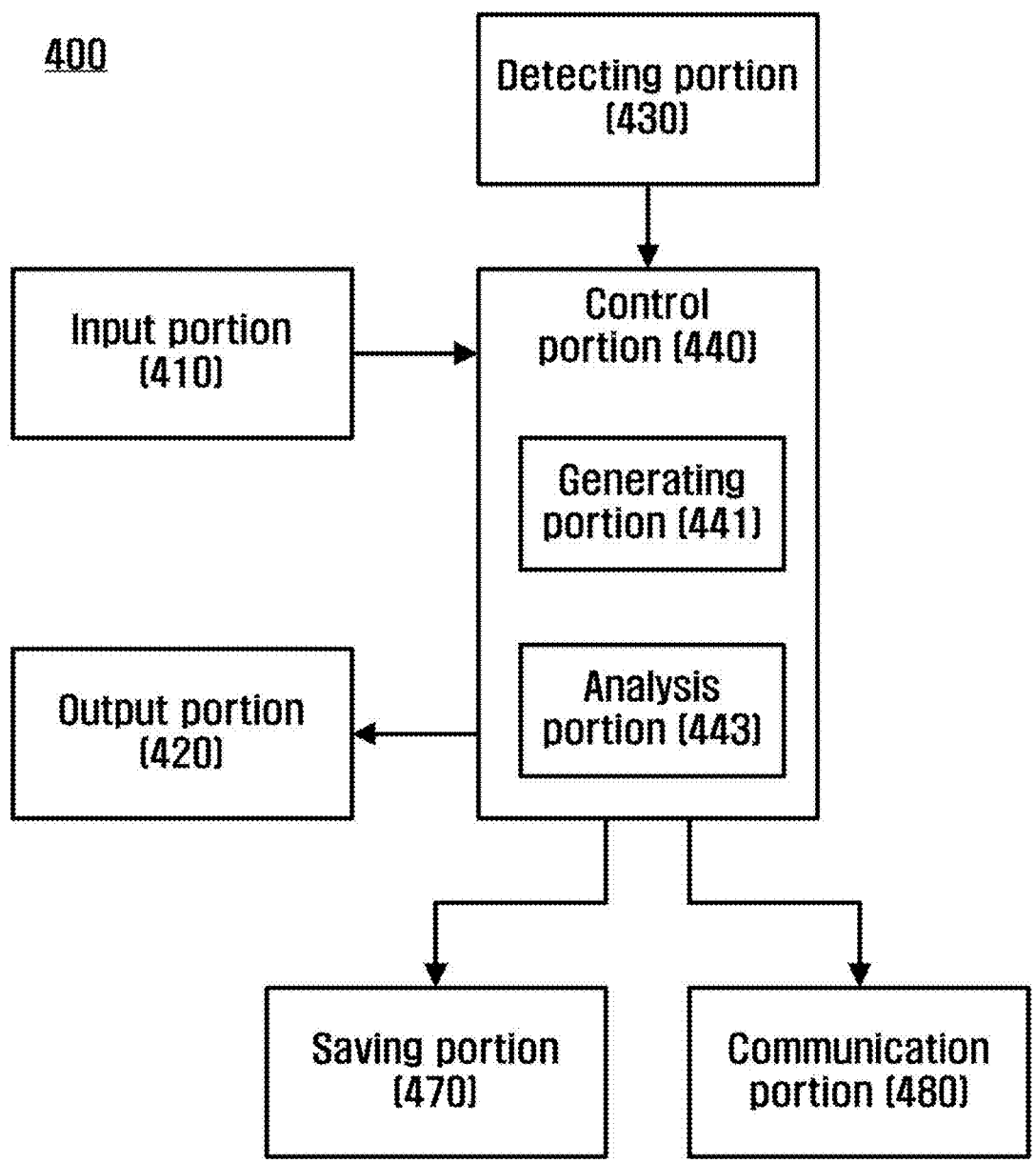
FIG. 6 is a diagram illustrating a composition of the first portable apparatus (400) of FIG.
Figure 7:
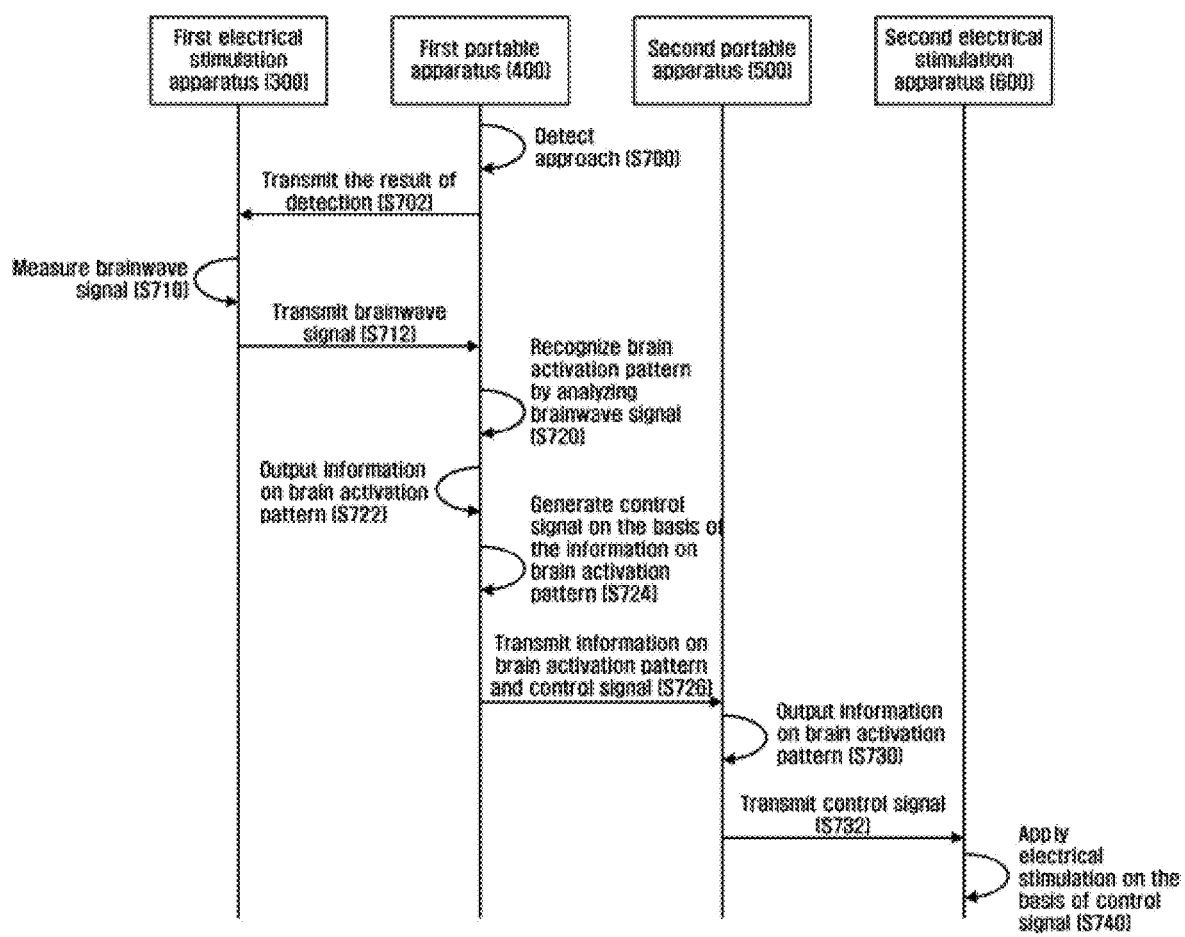
FIG. 7 is a flow chart illustrating one exemplary embodiment of the electrical stimulation method on the basis of the electrical stimulation system of TIG. 4.
Figure 8:
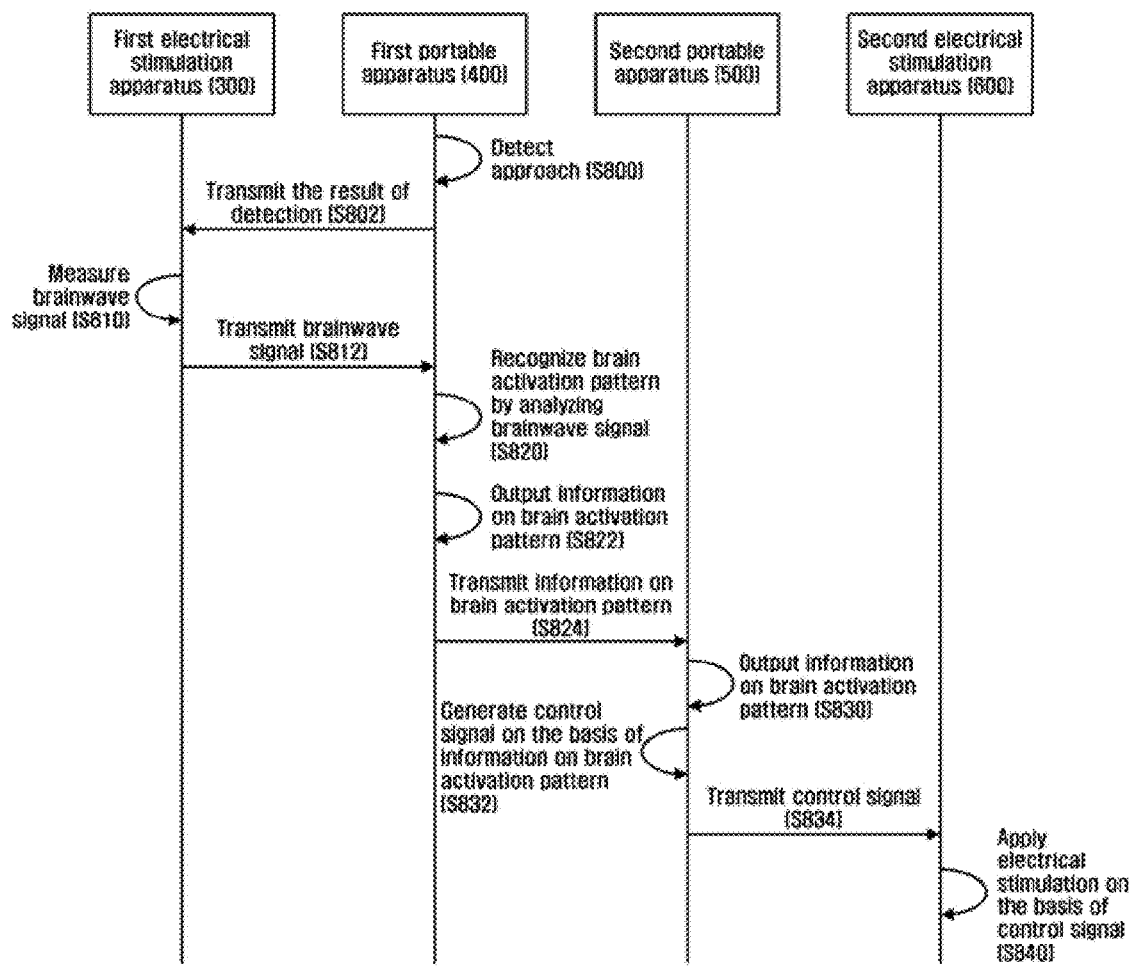
FIG. 8 is a flow chart illustrating another exemplary embodiment of the electrical stimulation method according to the electrical stimulation system of FIG. 4.

FIG. 5 is a diagram illustrating the accounting system and method according to further exemplary embodiment.

In reference with FIG. 5, the accounting system according to further exemplary embodiment may include the accounting processing apparatus (300) and the electrical stimulation apparatus (400).

The accounting processing apparatus (300) may include an input portion (340), an accounting processing portion (330), and a communication portion (310).

An input portion (340) can receive (S42) the information on the amount paid when the user (U) of the electrical stimulation apparatus (400) paid an appointed amount of rate (S41). In order for this, the input portion (340) may include a plurality of letter keys.

An accounting processing portion (330) can provide the amount paid by the user (U) to the manufacturer of the electrical stimulation apparatus (400). In addition, the accounting processing portion (330), on the basis of the information on the amount entered, can generate (S43) the information on the authority for use. For example, the information on the authority for use may include the information on the amount entered. For another example, the information on the authority for use may include the information on the kind of authority for use and its setting.

A communication portion (310) can transmit (S44) the information on the authority for use generated from the accounting processing portion (330) to the electrical stimulation apparatus (400). Particularly, the communication portion (310) can transmit the information on the authority for use generated by the accounting processing portion (330) to the electrical stimulation apparatus (400) in case the electrical stimulation apparatus (400) is contacted to the accounting processing apparatus (300) or near thereto within a certain range.

The electrical stimulation apparatus (400) can receive the information on the authority for use from the accounting processing apparatus (300) and operate (S45) according to the received information on the received authority for use.

For example, in case the information on the authority for use received from the accounting processing apparatus (300) includes the rate information, the electrical stimulation apparatus (400) can calculate the rate on the basis of the strength and the time for electrical stimulation applied whenever the user applies electrical stimulation by using the electrical stimulation apparatus (400), and deduct the amount calculated from the received rate information.

For another example, in case the information on the authority for use received from the accounting processing apparatus (300) includes the kind of authority for use and its setting, and more particularly, in case the kind of authority for use is related to the number of electrical stimulation which is set up as 10, the electrical stimulation apparatus (400) can deduct the set number for electrical stimulation one by one whenever the user applies electrical stimulation by using the electrical stimulation apparatus (400). Consequently, when the set number reaches 0, the electrical stimulation apparatus (400) may not operate anymore.

As above, the exemplary embodiments of the present invention were explained. In addition to the exemplary embodiments previously described, the exemplary embodiments of the present invention may also be embodied with a medium which includes a computer readable code/command, for example, a computer readable medium, to control at least one processing element among the exemplary embodiments previously described. The above mentioned medium can correspond to a medium/media enabling the saving and/or transmission of the computer readable code.

The computer readable code can be transmitted via internet as well as recorded to a medium, which includes, for example, a magnetic storage (such as ROM, floppy disk, and hard disk), an optical recording medium (such as CD-ROM, Blu-Ray, and DVD), and a transmission medium such as carrier wave. The above mentioned media may be a distributed network, and so the computer readable code can be saved, transmitted and operated by the distributed method. Moreover, for one example, a processing element may include a processor or a computer processor, and can be distributed and/or included in a device.

It is clearly understandable for those having ordinary skill in the art the present invention can be embodied in various forms, other than the exemplary embodiments set forth herein, without changes in its technical idea or essential characteristic. The exemplary embodiments described herein are only for the purpose of exemplifying the present invention in all aspects, not of limiting the scope of the present invention.

DESCRIPTION FOR REFERENCE NUMERALS

100, 300: First electrical stimulation apparatus
200, 600: Second electrical stimulation apparatus
400: First portable apparatus
500: Second portable apparatus

The invention claimed is:

1. An electrical stimulation system, comprising
an analysis unit configured to recognize a brain activation pattern of a first user by analyzing a brainwave signal of the first user measured by a first electrical stimulation apparatus; and
a stimulating unit configured to apply an electrical stimulation to the brain of a second user on the basis of the information on the recognized brain activation pattern of the first user,
wherein the first electrical stimulation apparatus includes a detecting unit configured to detect the second user's approach.

2. The electrical stimulation system of claim 1, wherein the result of detection by the detecting unit is used as an event signal for notifying the first electrical stimulation apparatus to start measuring the brainwave signal of the first user.

3. The electrical stimulation system of claim 1, wherein the analysis unit obtains a power spectrum about the brainwave signal of the first user, and recognizes the brain activation pattern of the first user on the basis of the obtained power spectrum.

4. The electrical stimulation system of claim 1, wherein the analysis unit is included in the first electrical stimulation apparatus.

5. The electrical stimulation system of claim 4, wherein the first electrical stimulation apparatus further includes a display unit configured to display the information on the recognized brain activation pattern of the first user.

* * * * *